(12) United States Patent  
Rezaizadeh et al.

(10) Patent No.: US 7,807,102 B1  
(45) Date of Patent: Oct. 5, 2010

(54) DEVICE AND METHOD FOR DISINFECTING STETHOSCOPE HEADS

(75) Inventors: Houman Rezaizadeh, Toms River, NJ (US); Rasoul Rezaizadeh, Toms River, NJ (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/209,449

(22) Filed: Sep. 12, 2008

(51) Int. Cl.
*A61L 2/18* (2006.01)
(52) U.S. Cl. .................... 422/28; 222/634; 422/292
(58) Field of Classification Search ............... 222/398, 222/631, 634, 424.5, 409
See application file for complete search history.

(56) References Cited

U.S. PATENT DOCUMENTS

| | | | |
|---|---|---|---|
| 3,292,993 A | 12/1966 | Musso | |
| 3,342,544 A | 9/1967 | Curiel | |
| 3,765,573 A | 10/1973 | Landsman | |
| 3,943,951 A | 3/1976 | Spotz | |
| 4,844,299 A * | 7/1989 | Sekiguchi et al. | 222/94 |
| 4,997,629 A | 3/1991 | Marchand | |
| 5,074,322 A | 12/1991 | Jaw | |
| 5,641,464 A | 6/1997 | Briggs et al. | |
| 6,018,835 A | 2/2000 | Schonfeld | |
| 7,282,177 B2 | 10/2007 | Castaneda | |
| 7,282,186 B2 | 10/2007 | Lake, Jr. et al. | |
| 2004/0258560 A1 | 12/2004 | Lake, Jr. et al. | |
| 2008/0264827 A1 * | 10/2008 | O'Connell et al. | 206/756 |

* cited by examiner

*Primary Examiner*—Elizabeth L McKane
(74) *Attorney, Agent, or Firm*—Blank Rome LLP

(57) ABSTRACT

A device for disinfecting a head of a stethoscope has a receiver adapted to hold a supply of disinfecting agent. A dispenser that is mounted to reciprocate relative to the receiver has a receptacle for receiving the head of the stethoscope. The dispenser can communicate with the supply of disinfecting agent and deliver its disinfecting agent to the receptacle. By pressing the head of the stethoscope against the dispenser, disinfecting agent will pass from the receiver through the dispenser and onto the head of the stethoscope.

18 Claims, 6 Drawing Sheets

DEVICE AND METHOD FOR DISINFECTING STETHOSCOPE HEADS

BACKGROUND OF THE INVENTION

1. Field of the Invention

The present invention relates to stethoscopes, and in particular, to devices and methods for disinfecting them.

2. Description of Related Art

Stethoscopes are used by medical professionals to hear faint sounds inside a patient's body cavity; for example, a heartbeat, breathing, and the like. Abnormalities in such sounds can reveal a disease. Stethoscopes are a traditional diagnostic instrument and have been used by medical personnel since the 19th century.

The head of a conventional stethoscope has an open bell on one side and on the other side a relatively wide and shallow chamber covered with a diaphragm. The side selected may be chosen based on the audio spectrum or other characteristics of the sound source. The stethoscope head communicates acoustically with a flexible tube that is joined through a Y union to a pair of tubes that connect to two earpieces in order to deliver binaural sound. The rims of the stethoscope's diaphragm and bell are typically circular, although in some cases a rim may be almond-shaped.

A risk of spreading infection with the stethoscope exists because of its routine use by professionals throughout the day on multiple patients. Nosocomial infections are a significant known cause of hospital morbidity and mortality. To prevent the spread of infection, some professionals will wipe the head of their stethoscope after each use with a pad soaked in isopropyl alcohol. Also, the depth of the bell on the head of the stethoscope makes effective wiping difficult. A simple and cost effective way to prevent these infections from spreading would be highly valuable to health care professionals and their patients.

One study recommends as effective cleaning solutions for stethoscopes 70% isopropyl alcohol or hypochlorous acid in solution. Africa-Purino, Edwin and Coronel, Stethoscopes: A Potential Source of Nosocomial Infections, The Philippine Journal of Microbiology and Infectious Diseases; Vol 29, No. 1, Topic 2 (January-March 2000). This study found that stethoscopes could harbor Staphylococcus aureus and other harmful and potentially lethal bacteria. This study also found that only about X % of medical professionals actually wipe the stethoscope after each use.

See also U.S. Pat. Nos. 3,292,993; 3,342,544; 3,765,573; 3,943,951; 4,997,629; 5,074,322; 5,641,464; 6,018,835; 7,282,177; and 7,282,186, as well as US Patent Application Publication No. 2004/0258560.

SUMMARY OF THE INVENTION

In accordance with the illustrative embodiments demonstrating features and advantages of the present invention, there is provided a device for disinfecting a head of a stethoscope. The device has a receiver adapted to hold a supply of disinfecting agent, and a dispenser. The dispenser is mounted to reciprocate relative to the receiver. The dispenser has a receptacle for receiving the head of the stethoscope. The dispenser is adapted to communicate with the supply of disinfecting agent and deliver its disinfecting agent to the receptacle.

In accordance with another aspect of the invention, a device is provided for disinfecting a head of a stethoscope. The device has a container containing a quantity of disinfecting agent. Also included is a dispenser that is reciprocatably mounted on the container. The dispenser has a converging receptacle for receiving the head of the stethoscope. The dispenser can communicate with the container in order to deliver its disinfecting agent to the receptacle in response to depression of the dispenser.

In accordance with yet another aspect of the invention, a method is provided for disinfecting a head of a stethoscope with a dispenser and a receiver holding a supply of disinfecting agent. The method includes the step of pressing the head of the stethoscope against the dispenser to depress it. Another step is passing the disinfecting agent from the receiver through the dispenser and onto the head of the stethoscope.

By employing apparatus and methods of the foregoing type, improved hygiene can be achieved when using a stethoscope. In a disclosed embodiment a cylindrical holder holds a container filled with a disinfecting agent such as isopropyl alcohol. The container can be pressurized, in which case depression of a tubular valve stem will dispense the disinfecting agent. Alternatively, the container may have a pump mechanism, wherein reciprocation of a tubular stem will pump the disinfecting agent from the container.

A spray fitting can be placed on the container's tubular stem in order to connect to a dispenser. In the depicted embodiment the dispenser is a cylindrical component that is slidably mounted in the upper end of the holder. By depressing the dispenser, once or repeatedly, disinfecting agent can be delivered from the container to a funnel-shaped receptacle on the upper exposed end of the dispenser. Accordingly, a stethoscope head placed into the receptacle can be pressed to cause the disinfecting agent to be sprayed into the receptacle and against the stethoscope head. In some embodiments, an optional absorbent pad mounted on the side of the holder can be used to wipe excess disinfecting agent from the stethoscope head.

In some cases the device can be placed on a countertop. In one disclosed embodiment, the device can be held in a mounting fixture. The fixture has a rear wall that can be attached to a vertical surface. A horizontal platform projecting from the rear wall has a domed protrusion that can fit into a mating hole on the bottom of the holder holding the container with the disinfecting agent. The disclosed mounting fixture has on its rear wall a hook that can hook into a mating slot on the side of the holder. This mounting fixture has one or more sidewalls that can be fitted with a wiping pad for wiping excess disinfecting agent from the stethoscope head.

BRIEF DESCRIPTION OF THE DRAWINGS

The above brief description as well as other objects, features and advantages of the present invention will be more fully appreciated by reference to the following detailed description of illustrative embodiments in accordance with the present invention when taken in conjunction with the accompanying drawings, wherein.

DETAILED DESCRIPTION OF THE PREFERRED EMBODIMENTS

Figure 1:
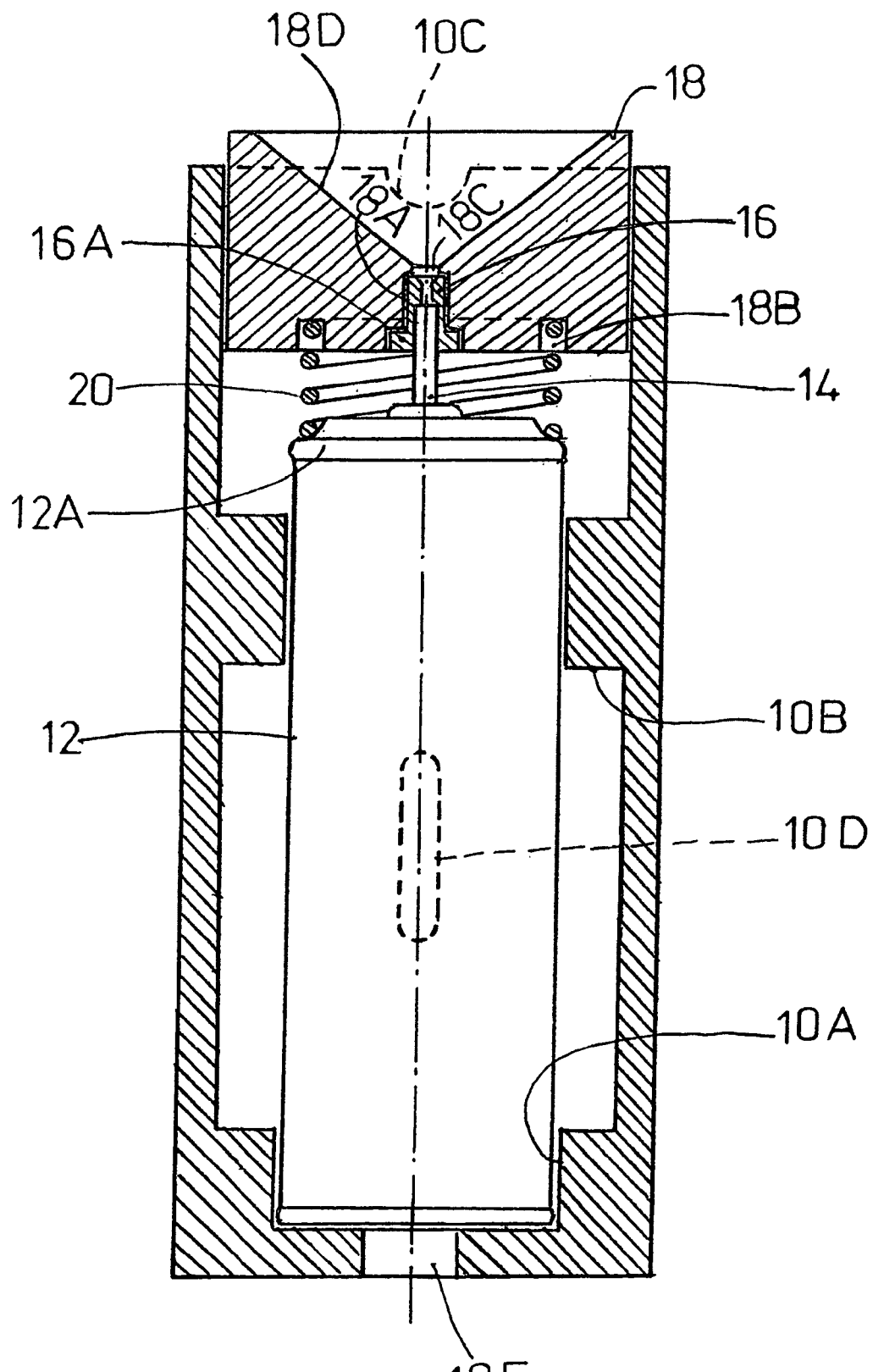
FIG. 1 is an elevational view, partly in section, of a device in accordance with principles of the present invention.
Figure 2:
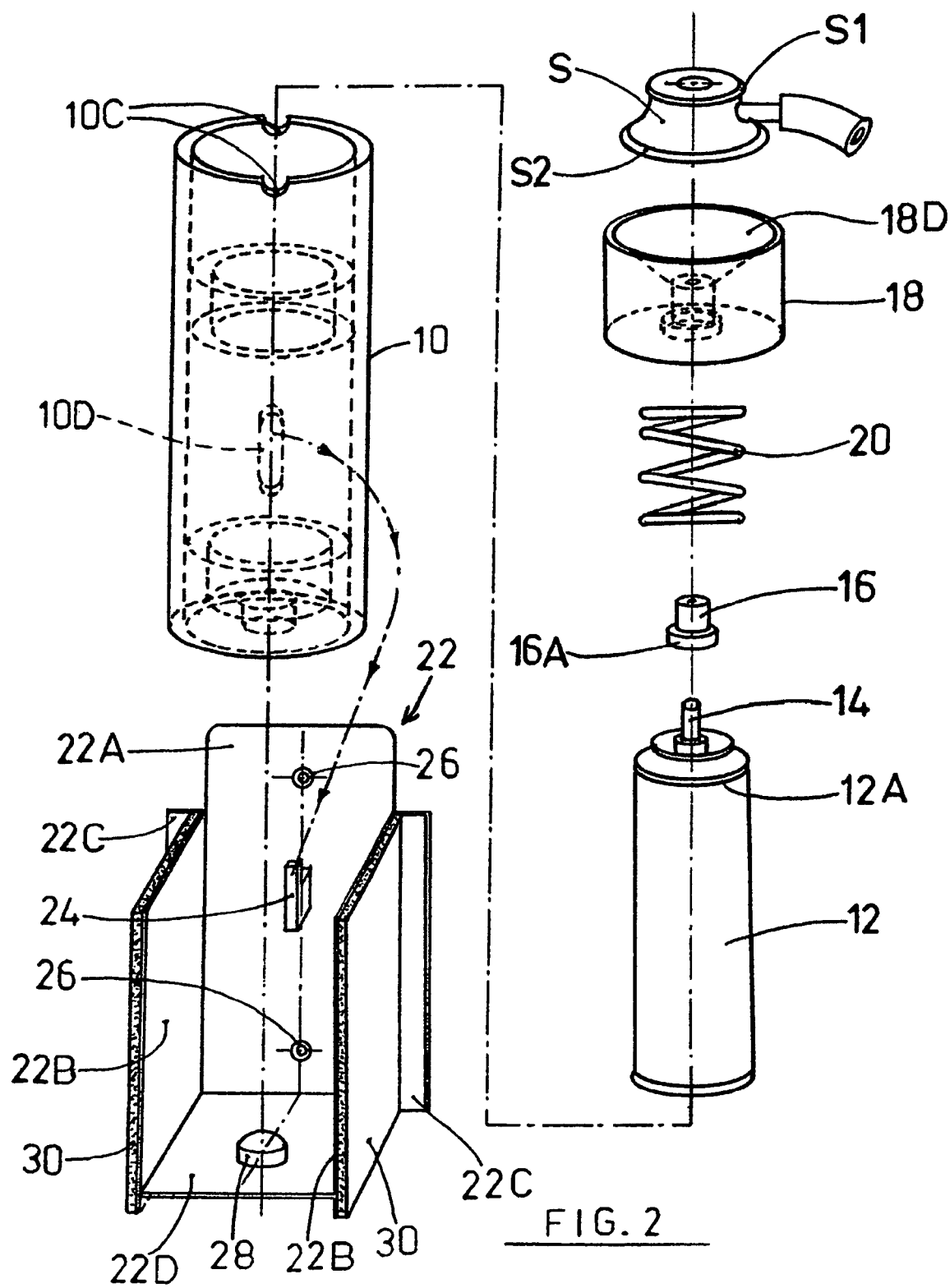
FIG. 2 is an exploded, perspective view of the device of FIG. 1 showing an optional mounting fixture.

Referring to FIGS. 1-4, a device for disinfecting the head of a stethoscope is shown as a hollow cylindrical holder 10 sized to hold a container 12 containing a supply of disinfecting agent. Holder 10 is also referred to as a receiver. Container 12 contains isopropyl alcohol at a concentration of 70% or greater, although other concentrations and other types of disinfecting agents are contemplated. For example, some embodiments may employ a solution of hypochlorous acid, or a solution of 2% chlorhexidine gluconate with 70% isopropyl alcohol (ChloraPrep™).

Container 12 has on top a tubular outlet 14 for delivering the container contents. In some embodiments outlet tube 14 may be part of a pump mechanism wherein reciprocation of tube 14 pumps out the disinfecting agent inside container 12 for delivery through the output tube. In some embodiments, container 12 may be pressurized with a gaseous propellant or otherwise, and outlet tube 14 may be part of a dispensing valve. In this case depression of outlet tube 14 will operate said valve to allow a pressurized release of the disinfecting agent inside the container 12 through the outlet tube 14.

The bottom of container 12 is shown fitted into a cylindrical socket 10A and the upper end of the container is surrounded by annular ridge 10B inside holder 10. In some embodiments socket 10A will be eliminated and the floor of holder 10 will be a simple flat surface. In any event, there is clearance between the side of container 12 and the inside of holder 10, which holder effectively forms a cylindrical sleeve around container 12.

Cylindrical port 16A of flanged tubular fitting 16 is pressed onto outlet tube 14 to communicate with passage 16B, which passage acts as a spray nozzle. Spray fitting 16, including its flange 16A is shown inside a matching cavity 18A of dispenser 18. Dispenser 18 is slidably fitted in the upper open end of holder 10 and rests upon helical compression spring 20. Spring 20 has an upper end mounted in annular groove 18B on the underside of dispenser 18 and a lower end mounted over the upper bead 12A of container 12. Being mounted in this fashion between dispenser 18 and container 12, spring 20 can upwardly urge dispenser 18. Dispenser 18 can be vertically lifted and removed by grasping it through a pair of diametrically opposed finger notches 10C on the upper rim of holder 10.

Figure 4:
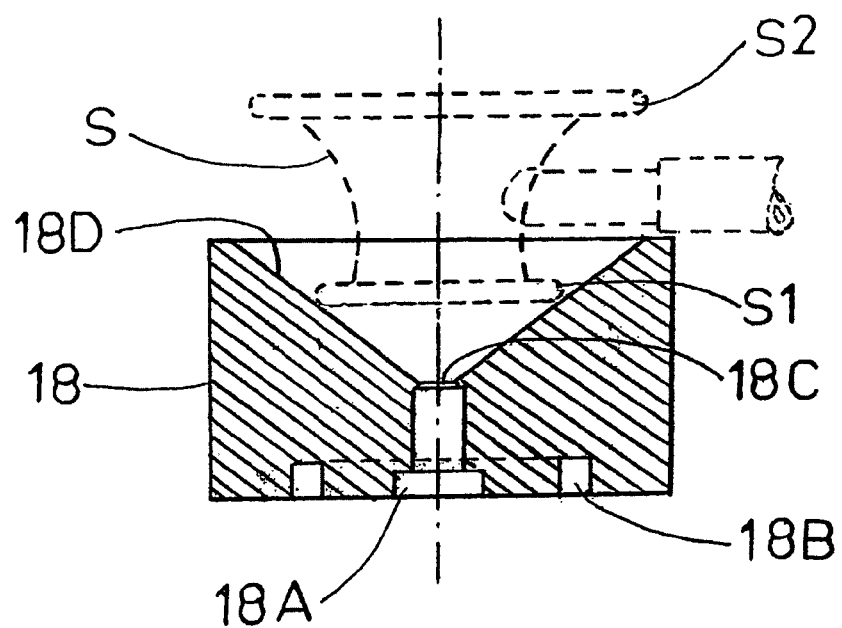
FIG. 4 is a vertical sectional view of the dispenser of FIG. 2.
Figure 3:
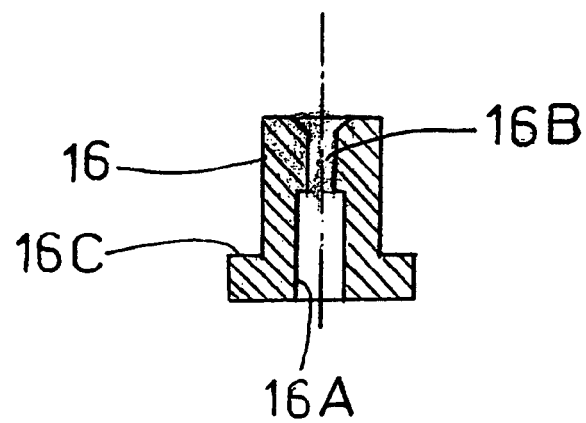
FIG. 3 is a vertical sectional view of the tubular fitting 16 of FIG. 2.

The upper, exposed end of dispenser 18 has a funnel-shaped, converging receptacle 18D communicating through a narrow mouth 18C to cavity 18A holding the fitting 16. In FIG. 4 the open bell S1 of stethoscope head S (illustrated in phantom) is shown pressed into receptacle 18D. While receptacle 18D is conical in this embodiment, in other embodiments the receptacle may be ellipsoidal, hemispherical, or have other cup shapes. While the surface of the receptacle 18D would usually be a surface of revolution, in some embodiments this surface may be axially asymmetric in order to accommodate a stethoscope head having an almond-shaped periphery.

Holder 10 has an optional, vertically oriented, side slot 10D sized to fit over L-shaped hook 24 on the outer face of mounting wall 22A of mounting fixture 22. A pair of holes 26 above and below hook 24 can be used to attach fixture 22 to a wall, although in some embodiments the fixture may be secured adhesively or by other means. Back wall 22A has a generally rectangular shape with rounded upper corners and has an opposite pair of flanges 22C projecting laterally from the lower four fifths of wall 22A. An opposing pair of sidewalls 22B project perpendicularly from wall 22A and are coterminous with the inside edges of flanges 22C. Platform 22D perpendicularly projects from back wall 22A and spans sidewalls 22B, slightly above the lower edges of the sidewalls. Dome-shaped protrusion 28 on platform 22D is sized to fit into a mating hole 10E in holder 10.

Mounted on the outside of sidewalls 22B are a pair of wiping pads 30 made of cloth, felt, absorbent paper or other absorbent material. Pads 30 are replaceable and can be attached by adhesive, hook and loop fasteners, or other means.

Figure 5:
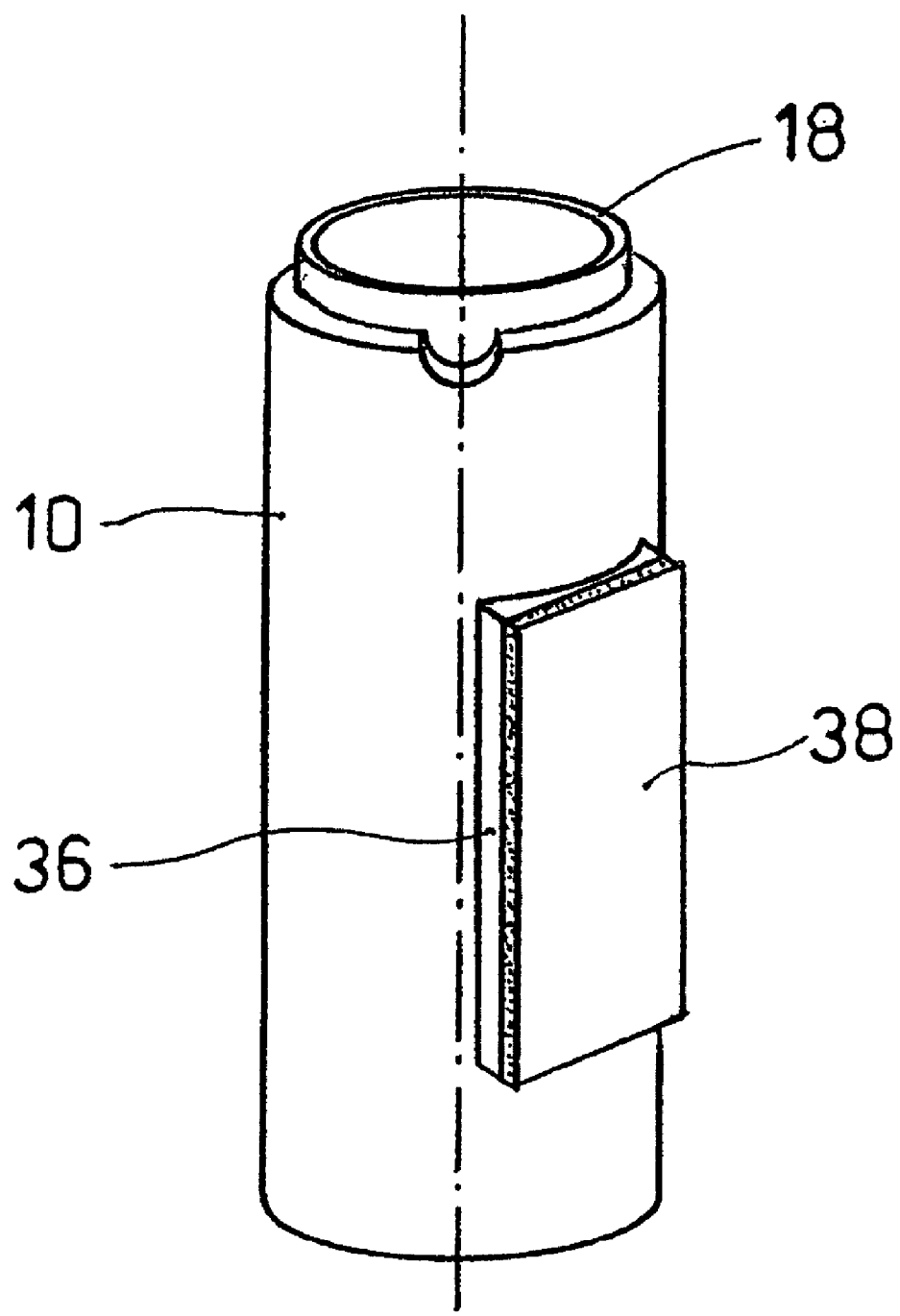
FIG. 5 is a perspective view of a device that is an alternate to that of FIG. 1 and modified to include a wiping pad.

Referring to FIG. 5, previously mentioned holder 10 was modified to include on its side a raised platform 36. Wiping pad 38 is mounted on the outside of platform 36. It will be appreciated that in some embodiments holder 10 will not have a separate platform, in which case wiping pad 38 may be mounted directly on the side of the holder.

Figure 6:
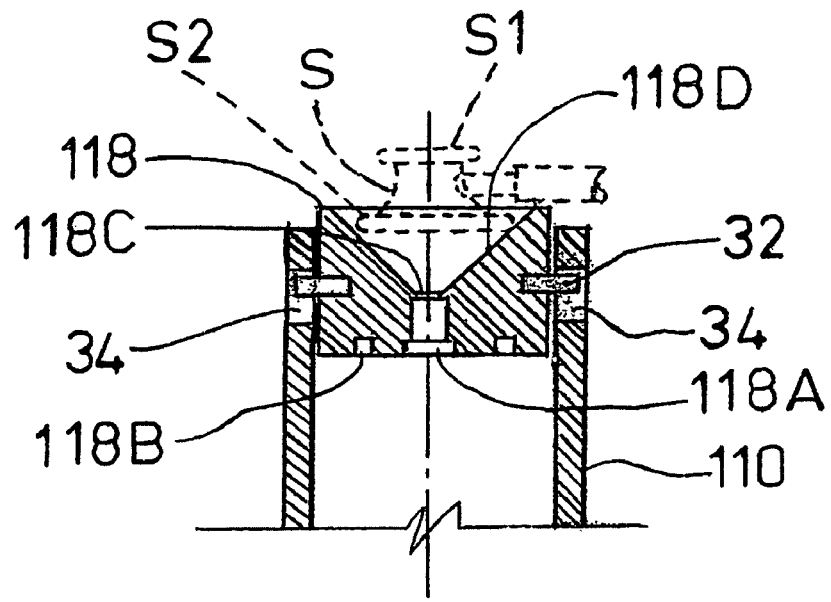
FIG. 6 is vertical sectional view of the upper portion of a device that is an alternate to that shown in FIG. 1.

Referring to FIG. 6, components corresponding to those previously illustrated in FIG. 1 bear the same reference numeral but increased by 100. Dispenser 118 is as before, but has an opposing pair of diametrically aligned pins 32 projecting into an opposing pair of slots 34 in holder 110. Accordingly, dispenser 118 can vertically reciprocate in holder 110 over a distance constrained by the length of slots 34. The wider side S2 of previously mentioned stethoscope head S (shown in phantom) has its diaphragm pressed against receptacle 118D in this view.

Figure 7:
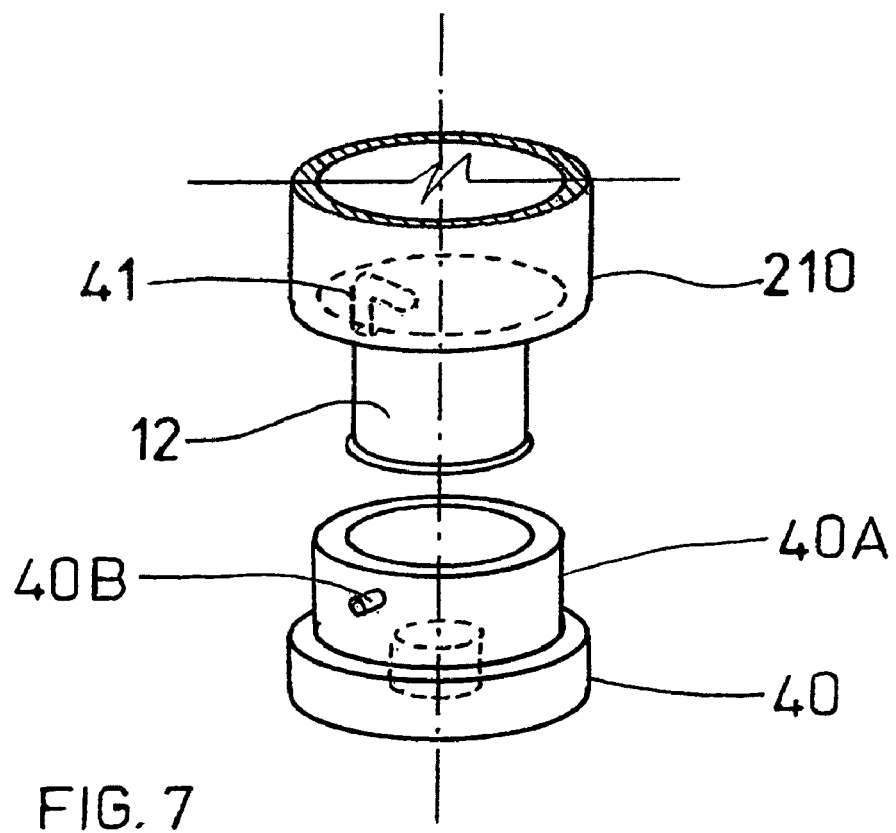
FIG. 7 is an exploded, perspective view of the lower portion of a device which is an alternate to that shown FIG. 1.

Referring to FIG. 7, holder 210 is constructed in a manner similar to the previously mentioned holder (holder 10 of FIG. 1), but here its bottom is open to receive previously mentioned container 12. The bottom of holder 210 can be closed with bottom closure 40. Closure 40 has a reduced diameter neck 40A with a diametrically opposing pair of stubs 40B designed to slide into an opposing pair of L-shaped grooves 41 on the inside of holder 210, thereby providing a bayonet coupling. Bottom closure 40 may be incorporated as a convenience feature, although for the embodiment of FIG. 5 closure 40 is greatly convenient since removal of dispenser 118 is difficult.

Figure 8:
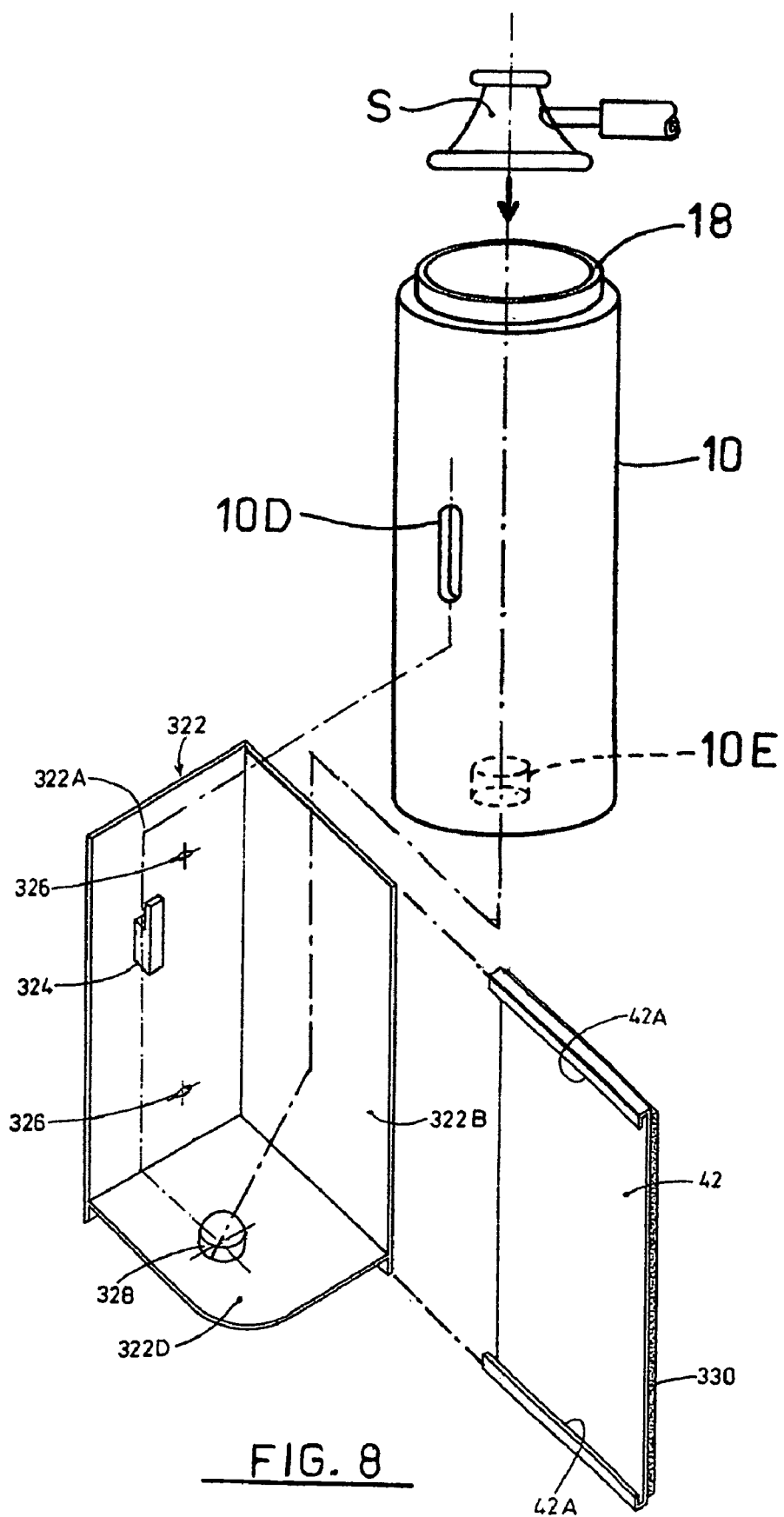
FIG. 8 is a perspective view of the device of FIG. 1 together with a mounting fixture, which fixture is an alternate that shown in FIG. 2.

Referring to FIG. 8, previously mentioned device 10/18 is shown about to be mounted on to an alternate mounting fixture 322. Components of fixture 322 corresponding to that previously described in connection with FIG. 2 bear the same reference numeral but increased by 300. As before, fixture 322 has a rear mounting wall 322A and a platform 322D with a domed protrusion 328. In this case however, fixture 322 only has a single right sidewall 322B.

A thin plastic panel 42 has curled edges 42A that slip over the top and bottom edges of sidewall 322B. Wiping pad 330 is permanently affixed to the outside of panel 42. As before, holder 10 can be mounted in fixture 322 by placing its hole 10E over protrusion 328 and slipping its slot 10D onto hook 324.

To facilitate an understanding of the principles associated with the foregoing apparatus, its operation will be briefly described in connection with the embodiment of FIGS. 1-4. It will be appreciated that the other illustrated embodiments operate in a similar manner.

Device 10/18 will often be supplied empty, that is, without container 12. Accordingly, dispenser 18 may be grasped through finger slots 10C and removed together with spring 20. Container 12 may be supplied with fitting 16 pre-installed, although in some cases a reusable fitting can be placed on tube 14 of container 12. Container 12 is then inserted into holder 10 through ridge 10B and into socket 10A. Thereafter, spring 20 can be placed atop container 12 before placing dispenser 18 back into holder 10, allowing the upper end of spring 22 to fall into annular slot 18B.

In some cases an absorbent wiping pad (not shown) may be adhesively attached to the side of holder 10 (for FIG. 6 pad 38 may be placed on platform 36). However, in this instance a wiping pad is not placed on the holder since mounting fixture 22 has such a wiping pad 30.

Mounting fixture 22 may be mounted on the wall of various rooms in a hospital, doctor's office, clinic, or other such facilities. Fixture 22 may be installed with adhesives or by driving screws, nails of other fasteners through holes 26 (fixture 322 of FIG. 8 can be installed in a similar manner). It is expected that such mounting fixtures will be installed in multiple rooms, bedsides, and wherever one might expect to use a stethoscope. In some cases more than one mounting fixture 22 may be installed in a single room.

Each mounting fixture 22 will be supplied with its own device 10/18 with an internal container 12. Device 10/18 will be placed on the mounting fixture 22 by placing slot 10D over hook 24, simultaneously placing hole 10E over protrusion 28. It will be appreciated that fixture 22 might not be employed in some locations. In that case device 10/18 will simply be placed on a table or other convenient location.

A medical professional may now use stethoscope head S in the usual manner, typically by placing the stethoscope head against the patient's chest, back, neck, or other site. Stethoscope head S need not be covered with a bacteriostatic sleeve and therefore acoustic efficiency is not impaired.

When the examination of the patient is completed, the medical professional may place the stethoscope head S into receptacle 18D, with either the open bell S1 or the diaphragm S2 down, as applicable. It will be appreciated that holder 10 need not be removed from mounting fixture 22, although the holder can be removed and relocated in cases where a medical professional wishes to have the holder nearby. Such convenience may be desired where a series of patients will be seen at a single location that is not near to a mounting fixture 22.

Head S is then depressed, causing depression of dispenser 18, fitting 16, and tube 14. In the case where container 12 is pressurized, disinfecting agent will be propelled through tube 14 and sprayed by fitting 16 into receptacle 18D and against stethoscope head S. In the case where tube 14 is part of a pump mechanism, stethoscope head S will be pressed down rhythmically to reciprocate dispenser 18 together with fitting 16 and tube 14. Consequently, disinfecting agent will be pumped through tube 14 and sprayed through fitting 16 into receptacle 18D against stethoscope head S.

If a wiping pad was placed on holder 10, the user may now wipe stethoscope head S on that pad to remove excess disinfecting agent. In this case, however, the user will wipe stethoscope head S against either one of the pads 30 on mounting fixture 22. Flanges 22C will shield the underlying wall from marks or stains that might be caused by the stethoscope banging against the wall or by disinfecting agent being accidentally wiped or splashed onto the wall.

This process may be repeated until container 12 is exhausted. Thereafter, dispenser 18 may be grasped through finger notches 10C and withdrawn together with spring 20. Container 12 is then removed and discarded before a replacement container is installed in holder 10. In this case container 12 will be supplied with a new spray fitting 16. Next, spring 20 and dispenser 18 is reinstalled in the manner previously described. For the embodiment of FIG. 7 container 12 may be replaced by turning closure 40 so that studs 40B slide into the corner of grooves 41 before being pulled away (standard bayonet connection). Then a new container 12 (with a new spray fitting 16) can be installed in holder 210 before placing neck 40A back into holder 210 in order to slide stubs 40B through grooves 41 to lock closure 40 into place.

Pads 30 on mounting fixture 22 may be replaced as they become worn or soiled. For example, pads 30 may be peeled away from walls 22B before being replaced with new pads 30, which may be installed using an adhesive backing on the pad. This adhesive backing may be initially shielded by a removable paper covering. For the embodiment of FIG. 8, the old pad 330 may be removed by sliding panel 42 off wall 322B before installing a replacement pad 330 by sliding curled edges 42A over the top and bottom edges of wall 322B.

It is appreciated that various modifications may be implemented with respect to the above described embodiments. For example, container 12 may be fitted with a dispenser 18 without using holder 10 (in which case the container is itself a receiver). Instead of using a hook and lower protrusion, other mounting fixtures may hold the receiver using a cavity, closely fitting sidewalls, dovetail connections, a clip, or other means. Also, access to the container may be through a threaded lid or threaded bottom closure. Alternatively, the holder may be two pieces that are threaded together to hold the container. In some cases, the holder may have flanges or other means for directly mounting the holder to a vertical surface. In some cases the container's outlet stem will have enough strength so that the spring supporting the dispenser can be eliminated.

Obviously, many modifications and variations of the present invention are possible in light of the above teachings. It is therefore to be understood that within the scope of the appended claims, the invention may be practiced otherwise than as specifically described.

The invention claimed is:

1. A device for disinfecting a head of a stethoscope, comprising:
    a receiver adapted to hold a supply of disinfecting agent;
    a dispenser removably mounted to reciprocate relative to said receiver, said dispenser having a receptacle for receiving the head of the stethoscope, said dispenser being adapted to communicate with said supply of disinfecting agent and deliver its disinfecting agent to said receptacle; and
    a mounting fixture adapted for wall mounting, said mounting fixture including a wiping pad for wiping the head of the stethoscope.

2. A device according to claim 1 comprising:
    a wiping pad mounted on said receiver for wiping the head of the stethoscope.

3. A device according to claim 1 wherein said disinfecting agent includes isopropyl alcohol.

4. A device according to claim 1 wherein said receiver comprises:
    a container adapted to hold a quantity of disinfecting agent; and
    a holder for holding said container.

5. A device according to claim 4 wherein said container is pressurized.

6. A device according to claim 4 wherein said container includes a manual pump.

7. A device according to claim 4 wherein said receptacle is funnel-shaped.

8. A device according to claim 7 comprising:
    a spring mounted under said dispenser for outwardly urging it.

9. A device according to claim 7 wherein said dispenser is releasably attached to said holder.

10. A device according to claim 7 comprising:
a tubular fitting connected between said container and said dispenser.

11. A device according to claim 4 wherein said holder comprises:
a sleeve; and
a bottom closure releasably connected to one end of said sleeve, the other end of said sleeve supporting said dispenser.

12. A device according to claim 1 wherein said wiping pad comprises:
a panel with an opposing pair of curled edges; and
an absorbent material mounted on said panel.

13. A device according to claim 1 wherein said receiver has a lower opening and a side slot, said mounting fixture having (a) a platform with a protrusion sized to fit in said lower opening, (b) a mounting wall with a hook sized to fit into said side slot, and (c) a sidewall with a wiping pad for wiping the head of the stethoscope.

14. A device according to claim 1 wherein said receptacle is funnel-shaped.

15. A device for disinfecting a head of a stethoscope, comprising:
a container containing a quantity of disinfecting agent;
a dispenser reciprocatably and removably mounted on said container, said dispenser having a converging receptacle for receiving the head of the stethoscope, said dispenser communicating with said container in order to deliver its disinfecting agent to said receptacle in response to depression of said dispenser; and
a mounting fixture adapted for wall mounting, said mounting fixture including a wiping pad for wiping the head of the stethoscope.

16. A method for disinfecting a head of a stethoscope using a dispenser, a receiver holding a supply of disinfecting agent, and a mounting fixture adapted for wall mounting that includes a wiping pad, the method comprising the steps of:
disposing a container with the supply of the disinfecting agent within the receiver;
pressing the head of the stethoscope against the dispenser to depress it;
passing the disinfecting agent from said container through said dispenser and onto the head of the stethoscope; and
wiping the head of the stethoscope with the wiping pad.

17. A method according to claim 16 wherein said receiver has a holder for holding a container of disinfecting agent, the method including the steps of:
repeatedly depressing the dispenser with the head of the stethoscope in order to draw disinfecting agent from said container; and
replacing the container when depleted, with another fresh container.

18. A method according to claim 17 further comprising the step of:
mounting the mounting fixture in proximity to said receiver.

* * * * *